(12) United States Patent
Steinkamp

(10) Patent No.: US 7,174,094 B2
(45) Date of Patent: Feb. 6, 2007

(54) SYSTEM AND METHOD FOR REFLEX-FREE COAXIAL ILLUMINATION

(76) Inventor: Peter Norman Steinkamp, 2712 SE. Woodward St., Portland, OR (US) 27202

(*) Notice: Subject to any disclaimer, the term of this patent is extended or adjusted under 35 U.S.C. 154(b) by 174 days.

(21) Appl. No.: 11/052,993

(22) Filed: Feb. 7, 2005

(65) Prior Publication Data
US 2006/0177205 A1    Aug. 10, 2006

(51) Int. Cl.
A61B 3/10 (2006.01)
G03B 29/00 (2006.01)

(52) U.S. Cl. .................. 396/18; 348/78; 351/207; 351/221; 362/235

(58) Field of Classification Search .............. 396/18; 348/78; 351/207, 213, 221; 362/235, 241
See application file for complete search history.

(56) References Cited

U.S. PATENT DOCUMENTS

| | | | |
|---|---|---|---|
| 3,594,071 A | 7/1971 | Okajima | |
| 3,914,032 A | 10/1975 | Takano et al. | |
| 4,176,920 A | 12/1979 | Ito | |
| 4,439,024 A * | 3/1984 | Ito | 351/207 |
| 4,784,483 A * | 11/1988 | Holladay et al. | 351/243 |
| 5,455,644 A | 10/1995 | Yazawa et al. | |
| 5,668,621 A | 9/1997 | Nanjo | |
| 5,671,039 A * | 9/1997 | Grolman | 351/243 |
| 5,684,626 A | 11/1997 | Greenberg | |
| 5,745,308 A | 4/1998 | Spangenberg | |
| 5,914,771 A | 6/1999 | Biber | |
| 6,474,837 B1 | 11/2002 | Belliveau | |
| 6,490,365 B2 * | 12/2002 | Horiguchi et al. | 382/117 |
| 6,637,882 B1 | 10/2003 | Goldfain et al. | |
| 6,755,526 B2 | 6/2004 | Shibata | |
| 6,755,882 B2 | 6/2004 | Otani et al. | |
| 7,048,379 B2 * | 5/2006 | Miller et al. | 351/213 |
| 2005/0041207 A1 | 2/2005 | Miller | |

* cited by examiner

Primary Examiner—W. B. Perkey
(74) Attorney, Agent, or Firm—Frank Stephen Michels

(57) ABSTRACT

A system is provided for reflex-free coaxial illumination that includes an objective lens group having an optical axis. An illumination source is axially disposed from the objective lens. The illumination source provides at least one light beam. The light beam is directed across the optical axis through a peripheral section of the objective lens. The light beam form a continuous field of illumination at a subject. A reflex mask is disposed behind the illumination source.

19 Claims, 5 Drawing Sheets

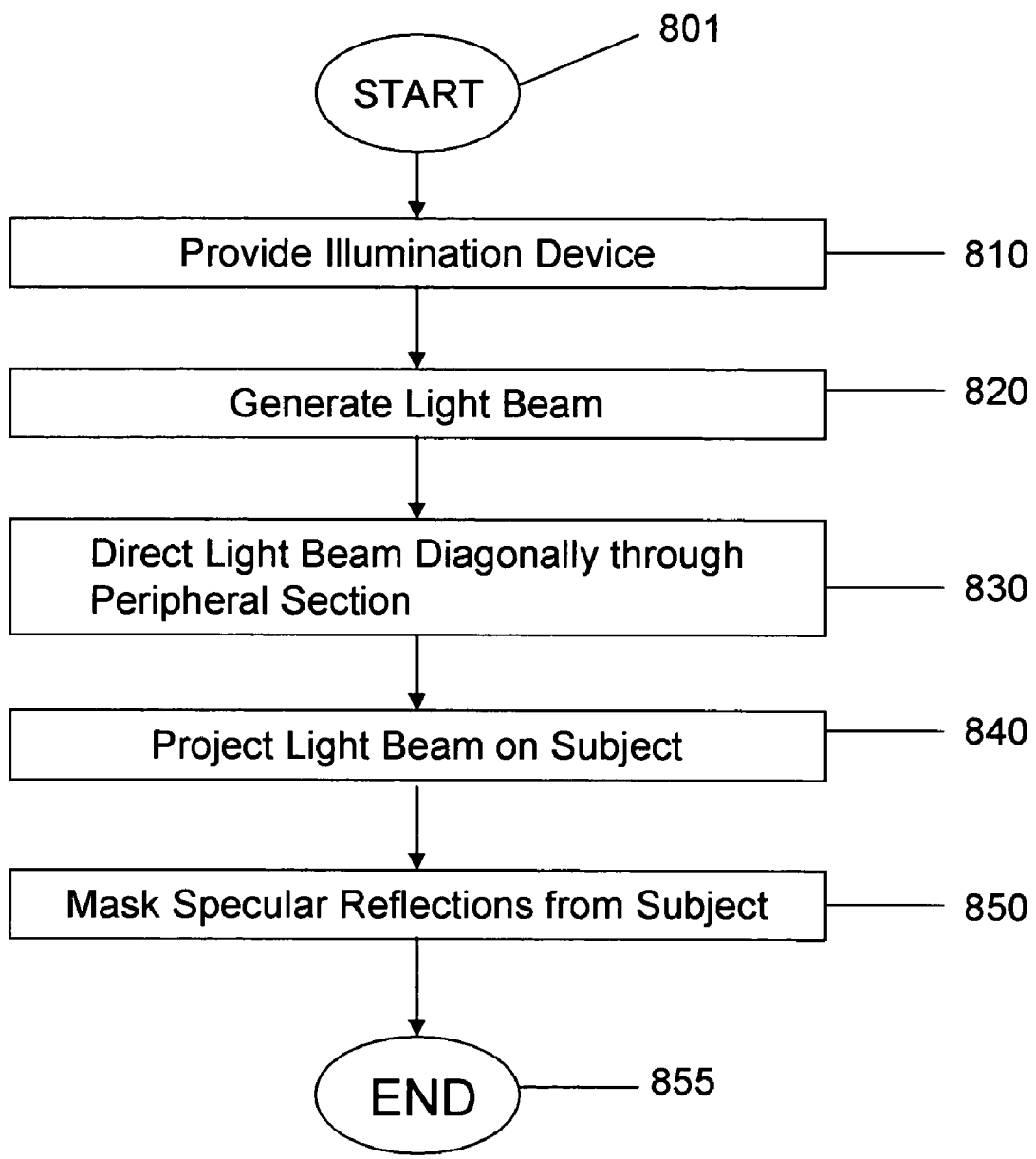

SYSTEM AND METHOD FOR REFLEX-FREE COAXIAL ILLUMINATION

FIELD OF THE INVENTION

This invention relates generally to coaxial illumination systems. In particular, the invention relates to system and method for reflex-free coaxial illumination in a viewing device.

BACKGROUND OF THE INVENTION

Coaxial illumination where illuminating light passes through a lens system that also forms the image of the subject is used in examination and viewing equipment. An annular shaped illumination device illuminates a subject while the subject is viewed through the center aperture of the annulus.

The retinal surface of the eye poses a unique challenge in illuminating and imaging. Light must be introduced through the pupil of the eye along the same axis as that of the imaging system. To achieve optimal imaging and viewing of the retinal surface, light must introduced without striking the central anterior structures of the eye, including the cornea and lens. Various means for eliminating reflections from these structures have been employed.

The use of a ring shaped illumination pattern is well known for eliminating reflections from the surfaces of the cornea and lens of the eye. This has been achieved with the use of light projection masks within the illumination and imaging sub-systems. Elimination of reflections from the rear surface of the objective lens has been achieved with beam splitting devices, polarized filters, projection masks and opaque spots applied directly to the rear surface of the objective lens. Although effective, these methods suffer from visible artifacts, light reduction or complex construction. Further, several prior retinal camera and ophthalmoscope designs utilize mirrors or beam splitting devices that must be held in very close proximity to the eye, risking unwanted contact.

Most ophthalmic devices generally utilize separate illumination and imaging paths, placing the illuminating light relatively distant from the objective lens. This arrangement necessitates the use of high wattage filament bulbs for viewing and xenon flash tubes for photographic imaging.

Presently available portable retinal cameras rely on wall current for operation and have not generally been used as examination devices because of their relatively large size.

It is therefore desirable to provide a system and method for reflex-free coaxial illumination that overcomes the limitations, challenges, and obstacles described above.

SUMMARY OF THE INVENTION

One aspect of the present invention provides a system for reflex-free coaxial illumination that includes an objective lens group having an optical axis. An illumination source is axially disposed from the objective lens. The illumination source provides at least one light beam. The light beam is directed across the optical axis through a peripheral section of the objective lens. The light beam form a continuous field of illumination at a subject. A reflex mask is disposed behind the illumination source.

Another aspect of the present invention provides a system for reflex-free coaxial illumination that includes an objective lens system having an optical axis. An illumination source is axially disposed from the objective lens system. The illumination source includes means for providing lighting across the optical axis and through a peripheral of the objective lens system. The system includes means for excluding light from striking a central area of the objective lens. The system includes means for eliminating optical reflections.

A third aspect of the invention provides a method for reflex-free coaxial illumination. The method starts with providing an illumination device comprising an objective lens group and an illumination source, the objective lens group having an optical axis. At least one lights beam is generated. The light beam is directed diagonally wherein the light beams cross the optical axis and travel through a peripheral section of the objective lens group. The light beam is projected on a subject. Specular reflections from the subject are masked.

The aforementioned and other features and advantages of the invention will become further apparent from the following detailed description of the presently preferred embodiment, read in conjunction with the accompanying drawings. The detailed description and drawings are merely illustrative of the invention rather than limiting, the scope of the invention being defined by the appended claims and equivalents thereof.

BRIEF DESCRIPTION OF THE DRAWINGS

FIG. 8 is a flowchart of a method for reflex-free coaxial illumination, in accordance with one embodiment of the invention.

DETAILED DESCRIPTION OF THE PRESENTLY PREFERRED EMBODIMENTS

Figure 1A:
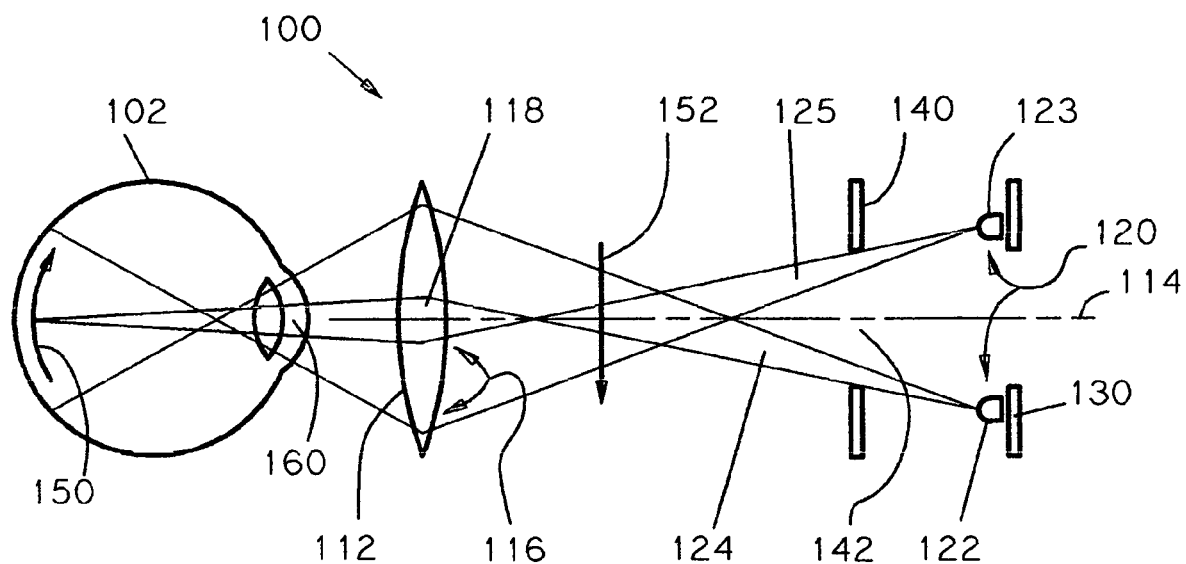
FIG. 1a is a schematic of one embodiment of a system for reflex-free coaxial illumination, in accordance with the present invention.

FIG. 1a is a schematic of one embodiment of a system for reflex-free coaxial illumination 100, in accordance with the present invention. The illumination system 100 is configured for illuminating a subject, such as the retinal surface 150 of an eye 102, allowing viewing of the retinal surface 150. Various optical components and imaging systems used for magnifying, inverting, relaying or recording an image 152 are not shown.

An objective lens group, consisting of at least one objective lens 112 and having an optical axis 114 is positioned in front of eye 102. An illumination mask 140 is placed between objective lens 112 and an illumination source 120. A reflex mask 130 is positioned behind illumination source 120.

Illumination source 120 is a ring-shaped illuminator consisting of at least one light-producing unit. Light-producing unit is a luminous body such as a light emitting diode (LED), a flash tube, a tungsten filament bulb, or a halogen bulb. Illumination source 120 is shown having a first light-producing unit 122 that emits a first light beam 124 and a second light-producing unit 123 that emits a second light beam 125. The two light producing units 122, 123 are positioned at opposing radial locations relative to optical axis 114 and project light beams 124, 125 diagonally across optical axis 114.

The two light beams 124, 125 pass through a center aperture 142 of illumination mask 140. Illumination mask 140 is configured to intercept a portion of light beams 124, 125 that is traveling in a path directed toward a central area 118 of objective lens 112. A minimal amount of light is blocked by illumination mask 140 preserving the available light for illumination of eye 102. Central area 118 is an area of objective lens 112 centered on optical axis 114.

The illumination mask 140 may be movable along the optical axis 114 to allow tuning of the light masking. As illumination mask 140 moves closer to objective lens 112, the unilluminated central area 118 decreases in size. Conversely, as the illumination mask 140 moves away from objective lens 112 the unilluminated central area 118 increases in size.

The two light beams 124, 125 travel across optical axis 114 and strike a peripheral section 116 of objective lens 112. Peripheral section 116 is a plurality of annular sections, or of circular segments of objective lens 112. The peripheral section 116 has a substantially annular shape thereby excluding central area 118 of objective lens 112. The size and position of peripheral section 116 is dependent on the relative positions of the other components of the system. Central area 118 remains unilluminated. Preventing light from striking central area 118 of objective lens 112 eliminates light reflex from the front and rear surfaces of the objective lens 112.

After light beams 124, 125 pass through peripheral section 116 of objective lens 112 they enter eye 102. Light enters the eye 102 remote from an apex 160 of eye 102, which is aligned with optical axis 114 and then are directed back across optical axis 114. The off-axis entry of the light into the eye 102 minimizes reflections from the cornea and the lens of the eye 102 returning back through objective lens 112. Off-axis entry of the light beams into the eye also reduces optical flare that may degrade visualization of the retinal surface 150 of eye 102. Specular reflections from the light producing units 122, 123 on the cornea and lens of eye 102 are negated by reflex mask 130. The use of reflex mask 130 is well known in the prior art of retinal cameras.

Light beams 123, 124 expand after entering eye 102 and merge at retinal surface 150 forming a field of continuous illumination. Light reflected from retinal surface 150 passes through objective lens 112 and inverted image 152 of retinal surface 150 is formed at the rear focal point of objective lens 112.

Multiple light-producing units may likewise be arranged where each provides illumination to part of the peripheral section of the objective lens disposed diagonally across the optical axis from the light-producing unit. The arrangement of light-producing units is such that the separate light beams exiting the objective lens combine by overlapping or joining to form a continuous field of illumination at the subject. A continuous ring of illumination, which may be regarded as of a multiplicity of light points, may also be utilized to achieve a similar effect.

Figure 1B:
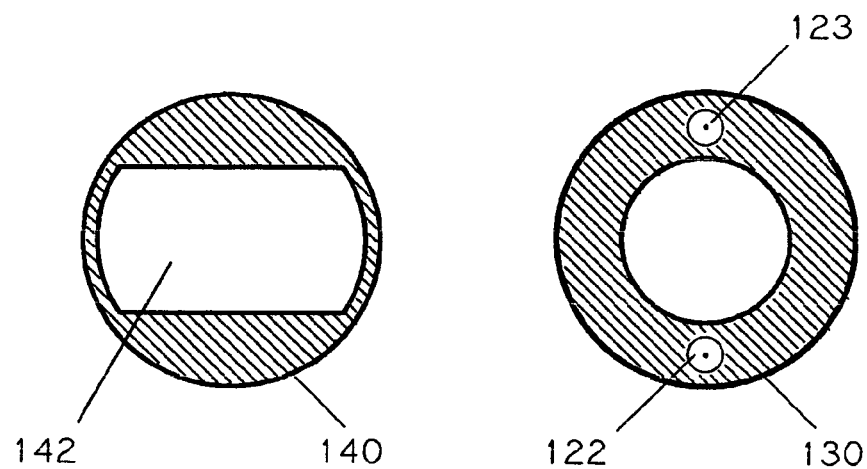
FIG. 1b is a schematic of the illumination source of FIG. 1a and its associated illumination mask, in accordance with the present invention.

FIG. 1b is a schematic of the illumination source of FIG. 1a and its associated illumination mask, in accordance with one embodiment of the invention. Illumination source 120 is shown having first light generating unit 122 and second light generating unit 123 positioned at opposing radial locations in front of reflex mask 130. Reflex mask 130 is shown shaped as an annulus. Illumination mask 140 includes linear shaped center aperture 142. Although a linear shaped center aperture 142 is the optimum aperture configuration used in conjunction with two light-producing units, various illuminator and masking configurations are possible provided that the projected light beams are excluded from the central area 118 of the objective lens 112 and upon exiting the objective lens, converge into a continuous field of illumination.

Figure 2:
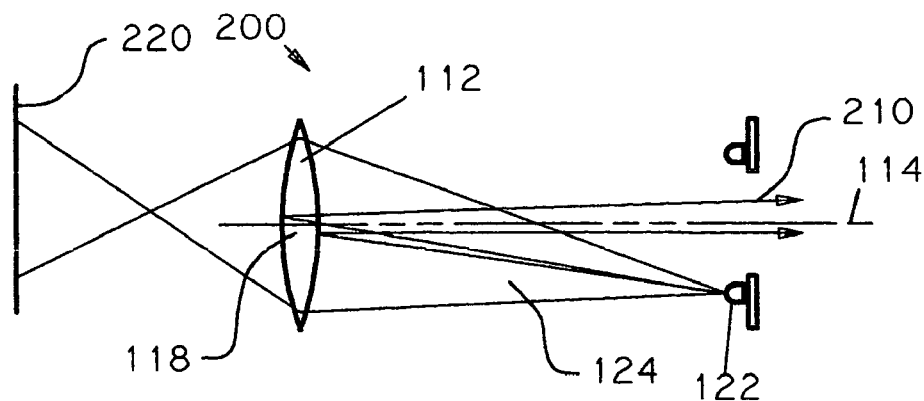
FIG. 2 is a schematic illustrating detrimental light reflex in a system for reflex-free coaxial illumination where an illumination mask is not used.

FIG. 2 is a schematic illustrating detrimental light reflex in a system 200 for reflex-free coaxial illumination where an illumination mask is not used. Where an illumination mask is not used, a portion of light beam 124 emitted by light generating unit 122 strikes the central area 118 of objective lens 112. Light striking central area 118 of objective lens 112 is reflected back along optical axis 114 producing a detrimental light reflex 210 and interfering with viewing a subject such as object 220. Detrimental light reflex 210 appears as a bright spot in the central area of the viewing field.

Figure 3:
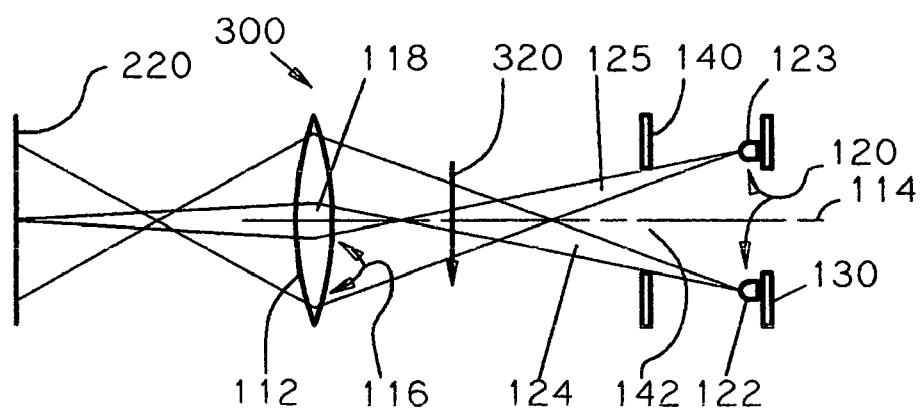
FIG. 3 is a schematic of an alternate embodiment of a system for reflex-free coaxial illumination, in accordance with the present invention.

FIG. 3 is a schematic representation of an alternate embodiment of a system 300 for reflex-free coaxial illumination, in accordance with the present invention. System for reflex-free coaxial illumination 300 is used for illuminating a subject other than the retinal surface such as object 220.

An objective lens group, consisting of at least one lens 112 and having an optical axis 114 is positioned in front of object 220. An illumination mask 140 is placed between objective lens 112 and an illumination source 120. A reflex mask 130 is positioned behind illumination source 120.

Illumination source 120 is a ring-shaped illuminator consisting of at least one light-producing unit. Light-producing unit is a luminous body such as an LED, flash tube, tungsten filament bulb, or halogen bulb. Illumination source 120 is shown having a first light-producing unit 122 that emits a first light beam 124 and a second light-producing unit 123 that emits a second light beam 125. The two light producing units 122, 123 are positioned at opposing radial locations relative to optical axis 114 and project light beams 124, 125 diagonally across optical axis 114.

The two light beams 124, 125 pass through a center aperture 142 of illumination mask 140. Illumination mask 140 is configured to intercept a portion of light beams 124, 125 that is traveling in a path directed toward a central area 118 of objective lens 112. A minimal amount of light is blocked by illumination mask 140 preserving the available light for illumination of object 220. Central area 118 is an area of objective lens 112 centered on optical axis 114.

The two light beams 124, 125 travel across optical axis 114 and strike a peripheral section 116 of objective lens 112. Peripheral section 116 is a plurality of annular sections, or of circular segments of objective lens 112. The peripheral section 116 has a substantially annular shape thereby excluding central area 118 of objective lens 112. The size and position of peripheral section 116 is dependent on the relative positions of the other components of the system.

Central area 118 remains unilluminated. Preventing light from striking central area 118 of objective lens 112 eliminates light reflex from the front and rear surfaces of the objective lens 112.

As light beams 124 travel through peripheral section 116 of objective lens 112 they are directed back across optical axis 114. Any reflections of light sources 122, 123 from the surface of object 310 that return through the objective lens 112 are blocked by reflex mask 130. Light beams 124, 125 expand and merge to form a continuous field of illumination at object 220. An inverted object image 320 is formed at the rear focal point of objective lens 112.

Figure 4:
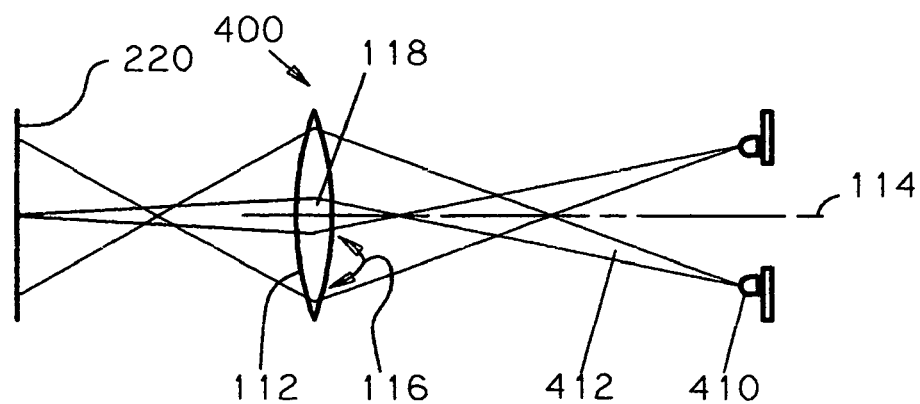
FIG. 4 is a schematic of a second alternate embodiment of a system for reflex-free coaxial illumination, in accordance with the present invention.

FIG. 4 is a schematic of an alternate embodiment of a system 400 for reflex-free coaxial illumination, in accordance with the present invention. The illumination mask 140 shown in FIG. 1 is removed in this embodiment. Removal of the illumination mask is enabled by using at least one light producing unit 410 that produces a light beam 412 with distinct borders, such as a low power laser or a partially collimated light source. The distinct borders of light beam 412 allow accurate placement of the incident light on objective lens 112 eliminating the need for masking. Light beam 412 provides illumination to peripheral section 116 of the objective lens 112 disposed diagonally across the optical axis 114 of the objective lens 112. The arrangement of multiple light-producing units is such that the separate light beams exiting the objective lens 112 combine by overlapping or joining to form a continuous field of illumination at the subject such as object 220. Light beam 412 is focused so that central area 118 of objective lens 112 remains unilluminated.

Figure 5:
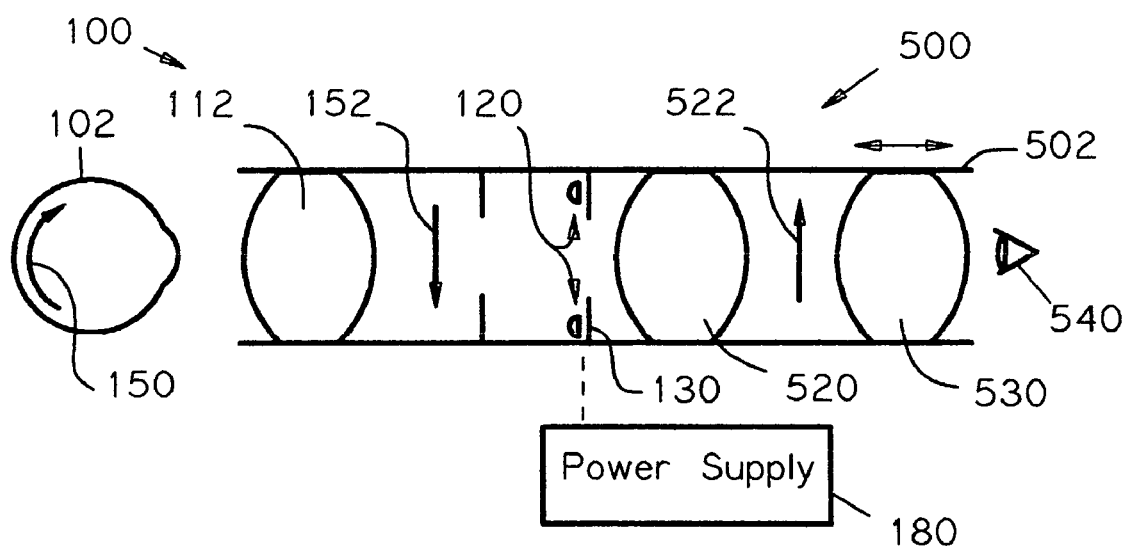
FIG. 5 is a schematic of one embodiment of a system for reflex free coaxial illumination used in conjunction with an ocular viewing system, in accordance with the present invention.

FIG. 5 is a schematic of one embodiment of a system for reflex free coaxial illumination 100 used in conjunction with an ocular viewing system 500, in accordance with the present invention. A support means, such as housing 502, encloses reflex free coaxial illumination system 100 and ocular viewing system 500. Ocular viewing system 500 includes a relay lens group 520 and an eye lens group 530 axially disposed behind reflex mask 130. Both lens groups 520, 530 include at least one lens. Subject is the retinal surface 150 of eye 102.

Light reflected from retinal surface 150 passes through the objective lens 112 and an inverted image 152 of retinal surface 150 is formed at the rear focal point of objective lens 112. A righted image 522 of retinal surface 150 is formed at the rear focal point of relay lens group 520. Eye lens group 530 is configured as needed for selected viewing of righted image 522. For example, eye lens group 520 is configured to magnify righted image 522 for direct viewing by an observer 540. Eye lens group 520 is movable, as shown by arrows, for focusing of righted image 522.

An illumination power unit 180 is operably connected to illumination source 120. Illumination power unit 180, which may be operated with portable electric sources or wall current, can be a standard power transformer or a programmable power controller. Illumination power controller 180 provides voltage required by illumination source 120. Where light control is needed, such as sequencing of the light-producing units or varying light intensity, a programmable power controller, such as a microcontroller, is coupled to the power transformer. Power controller 180 also has means for synchronization with imaging devices.

Figure 6:
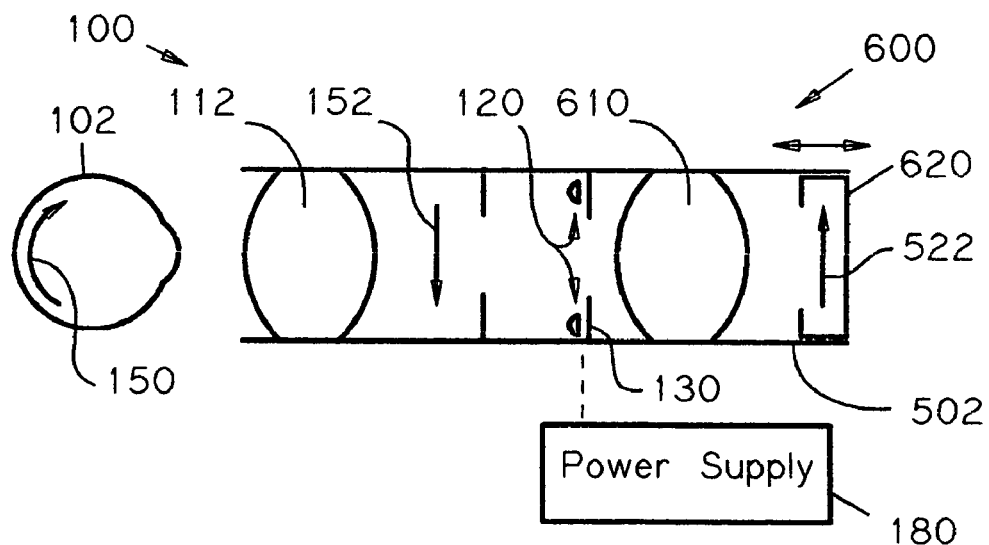
FIG. 6 is a schematic of one embodiment of a system for reflex free coaxial illumination used in conjunction with an imaging system, in accordance with the present invention.

FIG. 6 is a schematic of one embodiment of a system for reflex free coaxial illumination 100 used in conjunction with an imaging system 600, in accordance with the present invention. A support means, such as housing 502, encloses reflex free coaxial illumination system 100 and imaging system 600. Imaging system 600 includes a relay lens group 610 and an imaging device such as camera 620 axially disposed behind reflex mask 130. Relay lens group 610 includes at least one lens. Camera 620 is a film camera, a digital camera, or other image recording device. Subject is the retinal surface 150 of eye 102.

Light reflected from retinal surface 150 passes through the objective lens 112 and an inverted image 152 of retinal surface 150 is formed at the rear focal point of objective lens 112. A righted image 522 of retinal surface 150 is formed at the rear focal point of relay lens group 520. Camera 620 is configured as needed for selected imaging of righted image 522. In one example, camera 620 is configured to produce an image on photographic film. In another example, camera 620 is configured to produce a digitized image saved to a computer storage device, such as a hard drive.

An illumination power unit 180 is operably connected to illumination source 120 and is shown connected to camera 620. Illumination power unit 180, which may be operated with portable electric sources or wall current, can be a standard power transformer or a programmable power controller. Illumination power controller 180 provides voltage required by illumination source 120. Where light control is needed, such as sequencing of the light-producing units or varying light intensity, a means for power control, such as a microcontroller, is coupled to the power transformer. Power controller 180 also has means for synchronization with imaging devices, such as camera 620.

Figure 7:
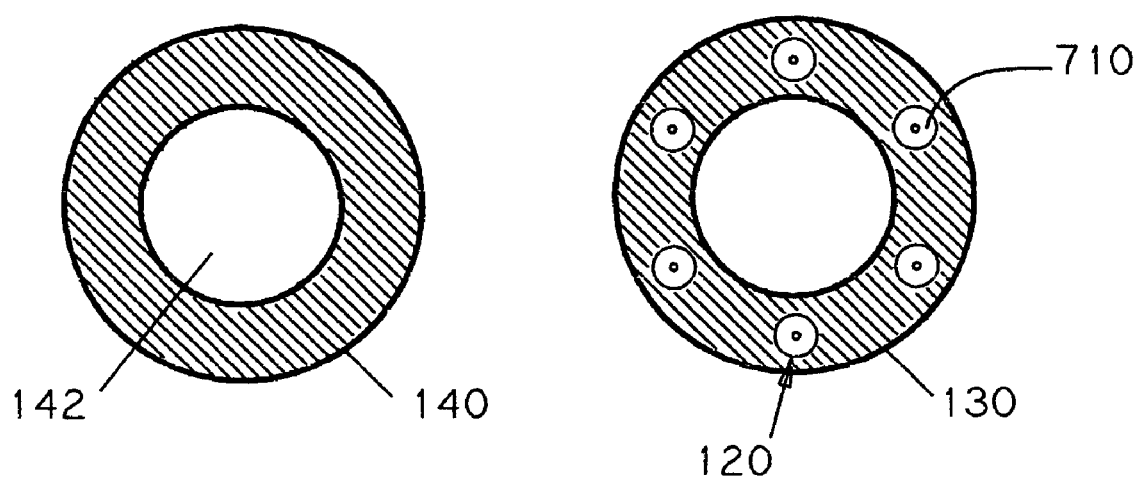
FIG. 7 is a schematic of an alternate illumination source and its associated illumination mask, in accordance with one embodiment of the invention.

FIG. 7 is a schematic of an alternate illumination source and its associated illumination mask, in accordance with one embodiment of the invention. Illumination source 120 is shown having a series of six LEDs 710 in a circular arrangement in front of reflex mask 130. Reflex mask 130 is shown shaped as an annulus. Center aperture 142 of Illumination mask 140 is circular. This configuration provides optimal masking of light emitted by each LED 710. In addition, the use of multiple light producing units allows the use of LEDs 710 of varying wavelengths. In one example, the system for reflex-free coaxial illumination is used in a non-mydriatic retinal camera. Both white light LEDs and infra-red LEDs are used. With an imaging camera sensitive to infra-red light, focusing and composition is accomplished using infra-red light from the infra-red LEDs. The final image is captured with a pulse of white light from the white light LEDs.

FIG. 8 is a flowchart of a method 800 for reflex-free coaxial illumination, in accordance with one embodiment of the invention. The method starts at step 801 and proceeds to provide an illumination device 100 including an objective lens group including at least one objective lens 112 and illumination source 120, at step 810. The objective lens group has optical axis 114. At step 820, at least one light beam is generated by the illumination source 120. At step 830, the light beam is directed diagonally so that the light beam crosses the optical axis 114 and travels through peripheral section 116 of the objective lens 112. At step 840, the light beam is projected on a subject, such as object 220. At step 850, specular reflections from the subject are masked. At step 855, the method terminates.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

What is claimed is:

1. A system for reflex free coaxial illumination comprising:
   an objective lens group, the objective lens group having an optical axis;
   an illumination source axially disposed from the objective lens group, the illumination source providing at least one light beam wherein the light beam is directed across the optical axis through a peripheral section of the objective lens group, the light beam forming a continuous field of illumination at a subject; and
   a reflex mask disposed behind the illumination source.

2. The system of claim 1 wherein the illumination source comprises a plurality of light-producing units.

3. The system of claim 1 further comprising an illumination mask disposed between the objective lens and the illumination source wherein the illumination mask prevents light from striking a central area of the objective lens group.

4. The system of claim 3 wherein the illumination mask includes an aperture, the aperture centered on the optical axis and sized to block a portion of the light beam traveling toward the central area of the objective lens group.

5. The system of claim 3 wherein the central area is centered on the optical axis.

6. The system of claim 3 wherein the illumination mask is movable along the optical axis.

7. The system of claim 1 further comprising a support means for enclosing the objective lens group, the illumination source and the reflex mask.

8. The system of claim 1 further comprising:
   a relay lens group axially disposed from the illumination source; and
   an eye lens group axially disposed from the relay lens group, the eye lens group moveable along the optical axis.

9. The system of claim 1 further comprising an imaging device axially disposed from the illumination source.

10. The system of claim 1 further comprising an illumination power unit operably connected to the illumination source.

11. The system of claim 10 wherein the illumination power unit includes means for power control; and means for synchronization with an imaging device.

12. The system of claim 1 wherein the reflex mask includes a circular aperture, the circular aperture centered on the optical axis and sized to block specular reflections of the illumination source.

13. The system of claim 1 wherein the illumination source includes a plurality of white light LEDs.

14. The system of claim 1 wherein the illumination source includes a plurality of infrared LEDs.

15. The system of claim 1 wherein the illumination source includes a plurality of LEDs, the LEDs having a plurality of light wavelengths.

16. A system for reflex-free coaxial illumination comprising:
   an objective lens group, the objective lens group having an optical axis;
   an illumination source axially disposed from the objective lens group, the illumination source including means for providing lighting across the optical axis and through a peripheral section of the objective lens group and means for excluding light from striking a central area of the objective lens group; and
   means for eliminating specular reflections of the illumination source.

17. A method for reflex-free coaxial illumination comprising:
   providing an illumination device comprising an objective lens group and an illumination source, the objective lens group having an optical axis;
   generating at least one light beam;
   directing the light beam diagonally wherein the light beams cross the optical axis and travel through a peripheral section of the objective lens group;
   projecting the light beam on a subject; and
   masking specular reflections from the subject.

18. The method of claim 17 further comprising: masking a portion of the light beams traveling toward a central area of the objective lens group.

19. The method of claim 17 further comprising: viewing an image of the subject.

* * * * *